United States Patent [19]
Gutowski et al.

[11] Patent Number: 5,171,666
[45] Date of Patent: Dec. 15, 1992

[54] MONOCLONAL ANTIBODIES REACTIVE WITH A CELL-SURFACE GYLCOPROTEIN EXPRESSED ON HUMAN CARCINOMAS

[75] Inventors: Magda C. Gutowski, Indianapolis; David A. Johnson, Carmel, both of Ind.

[73] Assignee: Eli Lilly and Company, Indianapolis, Ind.

[21] Appl. No.: 259,679

[22] Filed: Oct. 19, 1988

Related U.S. Application Data

[63] Continuation-in-part of Ser. No. 184,659, Apr. 22, 1988, abandoned.

[51] Int. Cl.$^5$ .............. C07K 15/28; C12N 5/20; G01N 33/574; G01N 33/577
[52] U.S. Cl. .............. 530/387.3; 435/70.21; 435/172.2; 435/240.27; 435/948; 435/7.23; 436/548; 436/813; 530/395; 530/806; 530/809; 530/828; 530/388.85; 530/861; 530/862; 530/864; 935/104
[58] Field of Search .............. 435/7, 172.2, 240.27, 435/948, 7.23, 7.25, 70.21; 436/518, 536, 543, 548, 813; 530/387, 395, 806, 809, 828; 935/104, 110

[56] References Cited

U.S. PATENT DOCUMENTS

| | | | |
|---|---|---|---|
| 4,132,769 | 1/1979 | Osther | 530/395 |
| 4,708,930 | 11/1987 | Kortright et al. | 435/7 |
| 4,713,352 | 12/1987 | Bander et al. | 436/811 |
| 4,800,155 | 1/1989 | Taniguchi et al. | 436/548 |
| 4,814,275 | 3/1989 | Durda et al. | 436/548 |
| 4,816,402 | 3/1989 | Rosen et al. | 436/548 |
| 4,816,567 | 3/1989 | Cabilly et al. | 935/15 |
| 4,912,031 | 3/1990 | Compton et al. | 435/7.23 |
| 5,019,497 | 5/1991 | Olsson et al. | 435/7.23 |

FOREIGN PATENT DOCUMENTS 0157613 3/1985 European Pat. Off. .

OTHER PUBLICATIONS

Mazauric et al., 1982, Cancer Research, 42: 150.
Brenner et al., 1982, Cancer Research, 42: 3187.
Mulshine et al., 1983, Journal of Immunology, 131(1): 497.
Masuko et al., 1985, Japanese Journal of Research, 76(5): 386.
Masui et al., 1986, Cancer Research, 46: 5592.
D. A. Johnson et al., Cancer Research, 50, 1790–1794, 1990.
W. W. Young, Jr. et al., Journ. Biol. Chem., 256, 10967–10972, 1981.
Boeheim et al., Int. Journ. Cancer, 36, 137–142 (1985).
Kimmel et al., Cancer Research, 46, 3614–3623 (1986).
Kyoizumi et al., Cancer Research, 45, 3274–3281 (1985).
Stahel et al., Biol. Abstr., 79, 87843 (1985).
Rosenblum et al., 1986, Hybridoma, 5(2): 117–127.

Primary Examiner—David A. Saunders
Attorney, Agent, or Firm—John E. Parrish; Leroy Whitaker

[57] ABSTRACT

The present invention relates to a novel tumor-associated antigen that is a cell-surface glycoprotein having a molecular weight in the range of 110,000–140,000 daltons that is present in a variety of carcinomas, including squamous cell carcinomas and adenocarcinomas. The invention also comprises antibodies reactive with the antigen, hybridoma cell lines that produce the antibodies of the invention, and methods for using the antibodies in the diagnosis and treatment of cancer.

20 Claims, 5 Drawing Sheets

MONOCLONAL ANTIBODIES REACTIVE WITH A CELL-SURFACE GYLCOPROTEIN EXPRESSED ON HUMAN CARCINOMAS

This application is a continuation-in-part of Ser. No. 07/184,659, filed Apr. 22, 1988 and now abandoned.

BACKGROUND OF THE INVENTION

The present invention relates to a novel tumor-associated antigen that is a cell-surface glycoprotein having a molecular weight in the range of 110,000–140,000 daltons and that is present in a variety of carcinomas, including squamous cell carcinomas and adenocarcinomas. The invention also comprises antibodies reactive with the antigen, hybridoma cell lines that produce the antibodies of the invention, and methods for using the antibodies in the diagnosis and treatment of cancer.

The lymphocyte hybridoma technique described by Kohler and Milstein (Nature 256:495–497, 1975) has enabled the isolation of monoclonal antibodies directed against a vast array of antigenic targets. Many laboratories have taken advantage of hybridoma technology to produce monoclonal antibodies which bind to tumor-associated antigens from a large number of tumor types, including tumors derived from lung, liver, colon, breast, kidney, bladder, skin, brain, prostate, and lymphocytes (reviewed by Sulfitzeanyu, 1985, Advances in Cancer Research 44:1).

Monoclonal antibodies reactive with tumor antigens have been used for a variety of diagnostic and therapeutic purposes. Monoclonal antibodies labeled in a variety of ways serve as useful reagents in the detection, diagnosis, and treatment of carcinomas. The particular labeling technique used to conjugate the antibody to the label depends on the purpose for which the conjugate was made. Fluorescent, radioactive, and enzymatic labels are commonly used to detect and diagnose disease states, while monoclonal antibodies designed for therapeutic purposes are often labeled with radioisotopes or chemical and biological agents. In all cases, the binding of a labeled monoclonal antibody to the appropriate antigen will signal detection of the cellular target or delivery of the conjugate to the cellular target.

Early diagnosis of malignancies and the identification of tumor-type is critical to the clinical management of carcinoma. The present invention comprises monoclonal antibodies reactive with an antigen expressed on human carcinoma cells. Although production of monoclonal antibodies reactive with carcinomas is described in U.S. Pat. No. 4,708,930; European Patent Publication 157,613; Mazauric et al., 1982, Cancer Research, 42:150; Brenner et al., 1982, Cancer Research, 42:3187; Mulshine et al., 1983, The Journal of Immunology, 13161:497; and Masuko et al., 1985, Japanese Journal for Cancer Research 76(5):386, no monoclonal antibodies reactive with the antigen of the present invention have been described. All squamous carcinomas of the lung, head, and neck, and adenocarcinomas of the colon and lung, express the antigen and therefore react with the antibodies of the invention. The broad distribution of the L/1C2 antigen on human carcinomas demonstrates the significant diagnostic and therapeutic applications of this invention.

SUMMARY OF THE INVENTION

The present invention is directed to a tumor-associated glycoprotein antigen in substantially pure form, said antigen having a molecular weight in the range of 110,000–140,000 daltons as determined using SDS-PAGE under reducing conditions; being present on the surface of human squamous carcinoma cells arising from epithelial cells of the head, neck, and lungs; and being susceptible to immunoprecipitation with the antibody produced by the hybridoma cell line L/1C2. A further aspect of the antigen of the invention is the finding that the L/1C2 antigen is internalized following the binding of antibodies of the invention. The internalization of the L/1C2 antigen is an important aspect of therapeutic embodiments of the instant invention in that it allows intracellular delivery of oncolytic agents, which have been linked to the antibodies of the invention, upon their binding to the L/1C2 antigen and the subsequent endocytosis of the antigen-antibody complex. The invention is also directed to a hybridoma cell line that produces an antibody reactive with the tumor-associated glycoprotein antigen set forth above. The present invention is also directed to the antibodies which are reactive with the tumor-associated glycoprotein antigen set forth above. The invention is also directed to a method of detecting the presence of L/1C2 antigen in a sample, which comprises adding to the sample the antibody which is reactive with the tumor-associated antigen set forth above, and measuring the reactivity of the antibody to the sample.

The antibodies of the invention are especially useful for delivering cytotoxic agents in vivo to tumors expressing the L/1C2 antigen. Cytotoxic agents demonstrate a significant increase in efficacy when attached to the antibodies of the invention.

BRIEF DESCRIPTION OF THE DRAWINGS

FIG. 1. SDS-PAGE analysis of L/1C2 antibody and antigen. Panel A: Coomassie blue stained 7–15% gradient gel run under reducing conditions showing single heavy and single light chains of protein A purified L/1C2 antibody. Panel B: Autoradiogram of immunoprecipitated $^3$H-glucosamine-labeled L/1C2 antigen analyzed on a 7–15% gel under reducing conditions alongside molecular weight standards. The numbers shown represent the molecular weight of the standard multiplied by $10^{-3}$. A myeloma IgG3 negative control did not immunoprecipitate identifiable antigens.

FIG. 3. The kinetics of the internalization of L/1C2 antibodies following binding to the L/1C2 antigen on T222 cells are revealed by UV microscopy. The details of this analysis appear in Example 10. Panel A reveals the bright ring-like fluorescence characteristic of membrane staining at the 0 time point. Panel B, which is a 105 minute time point, analysis reveals clusters of staining at the periphery of the cell. Panel C, the 135 minute time point reveals only intracellular staining indicating that the L/1C2 antibody has been internalized.

FIG. 4. The growth curves of T222 xenografts in the nude mouse xenograft model which is described in Example 12 are shown. Panel A demonstrates the efficacy of L/1C2-DAVLBHYD in suppressing the growth of T222 tumors. Panel B is a control group wherein DAVLBHYD was conjugated to an immunoglobulin which does not bind to the tumor cells. Panel C is a free drug control included to allow comparison of DAVLBHYD activity with the L/1C2 antigen reactive immunoconjugates of Panel A and non-L/1C2 antigen reactive immunoconjugates of Panel B.

DETAILED DESCRIPTION OF THE INVENTION

The present invention provides hybridoma cell lines that produce antibodies reactive with a glycoprotein antigen expressed on the surface of human carcinomas such as adenocarcinoma and squamous cell carcinoma. The antibodies produced by these hybridomas, together with the purified form of this novel tumor-associated antigen, are also important aspects of the invention.

The antigen, termed L/1C2, can be isolated by immunoprecipitation from extracts of human carcinoma cell-lines biosynthetically labeled with $^3H$ glucosamine. The L/1C2 antigen is a glycoprotein having a molecular weight in the range of 110,000 to 140,000 daltons as determined on a reducing SDS-PAGE gradient gel.

Hybridoma cell lines of the invention can be prepared using a cell-line of human carcinoma origin as immunogenic material for activation of immunologically relevant spleen cells. Spleen cells are then immortalized by fusion with mouse myeloma cells. The hybrid cells, called hybridomas, or hybridoma cell lines resulting from the fusion, are then selected and screened for reactivity with L/1C2 antigen presented on a variety of human carcinoma cell-lines, including those listed in Table 1, below.

TABLE 1

Representative Distribution of the L/1C2 Antigen on Human Carcinoma Cell-Lines

| Cell Line | Origin/Comments | Membrane Fluorescence |
|---|---|---|
| Squamous Carcinomas | | |
| FADU | Pharynx | + |
| ME180 | Cervix (epidermoid) | + |
| T222 | Lung | + |
| USCLS-1 | Lung | + |
| 5637 | Bladder | + |
| Transitional Cell Carcinomas | | |
| T24 | Bladder | + |
| RT4 | Bladder (papilloma) | + |
| J82 | Bladder | +/− |
| TCCSUP | Bladder | + |
| Adenocarcinomas | | |
| WiDr | Colon | + |
| HT29 | Colon | + |
| SK-CO-1 | Colon (ascites) | + |
| UCLA/P3 | Lung | + |
| DU145 | Prostate | + |
| PC3 | Prostate | +/− |
| Melanomas | | |
| M21 | Skin | − |
| M14 | Skin | − |
| Non-Transformed Cell Lines | | |
| FLOW 2000 | Fetal lung fibroblast | − |
| Detroit 551 | Skin fibroblast | − |

In Table 1, obvious membrane fluorescence is indicated by (+); weak fluorescence by (+/−); and negative reactivity by (−). All determinations are made relative to myeloma protein negative controls. Target cell lines included the following lines obtained from the American Type Culture Collection, Rockville, Md. 20852 ATCC: FaDu (ATCC #HTB43), 5637 (ATCC #HTB9), ME180 (ATCC #HTB33), SK-CO-1 (ATCC #HTB39), PC3 (ATCC #CRL1435) DU145 (ATCC #HTB81), T24 (ATCC #HTB4), RT4 (ATCC #HTB2), HT29 (ATCC #HTB38), J82 (ATCC #HTB1), TCCSUP (ATCC #HTB5), and WiDr (ATCC #CCL218). Other cell lines included; T222 (Masui, et al., 1984, Cancer:44(3) 1002–7), M14 (Chee et al., 1976, Cancer Research 36(4):1503–1509), UCLA/P3 (Varki et al., 1984, Cancer Research 44:681–687, and M21 (Morton et al., 1968, Surgery 64(1):233–240. Flow 2000 was obtained from Flow Laboratories, Inc., 7655 Old Springhouse Road, Mc-Lean, Va., 22101.

Figure 2:
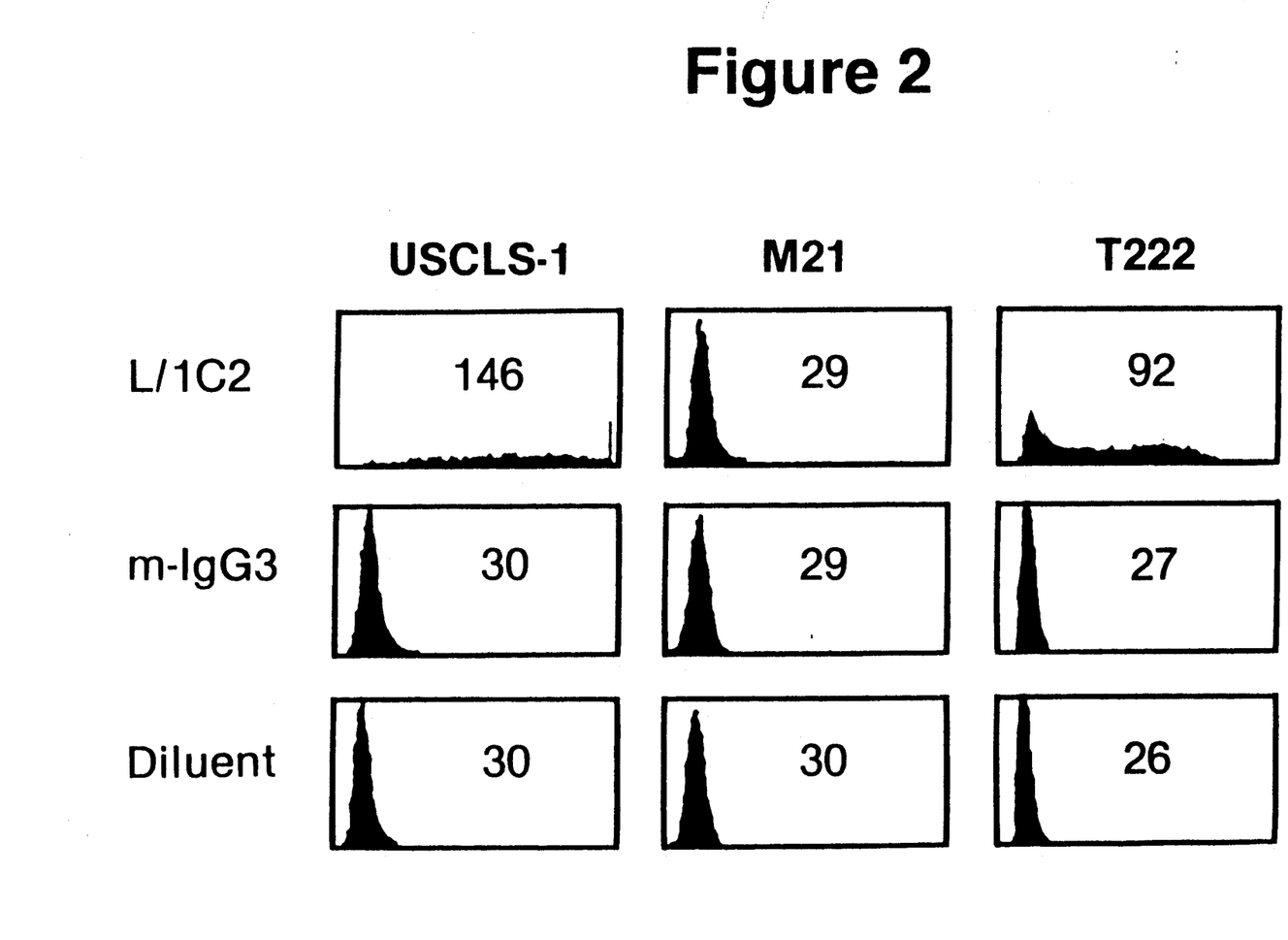
FIG. 2. Cell sorter analysis of L/1C2 reactivity with selected tumor cell lines. USCLS-1, M21, and T222 target cells were incubated in suspension with L/1C2 or a myeloma IgG3 control immunoglobulin (m-IgG3) as indicated. The detecting reagent was fluorescein labeled goat F(ab')$_2$ anti-mouse IgG and IgM. Mean channel fluorescence is indicated.

The broad distribution of the L/1C2 antigen on cell lines derived from tumors of epithelial origin is well represented in Table 1. The reactivity of antibodies of the invention with cell lines was assessed using an Epics-Coulter ® Mark IV ® cell analyzer (Coulter Electronics, Hialeh, Fl.) as per manufacturers methodology. Results of the flow cytometry analyses are illustrated in FIG. 2 of the accompanying drawings. Pathology samples of fresh human tumor and normal tissues were evaluated to illustrate the diagnostic methods of the invention. Normal tissue distribution of the L/1C2 antigen using the immunoperoxidase (an antibody-enzyme conjugate) method is described in Example 6.

Table 2 demonstrates the broad distribution of the L/1C2 antigen on carcinomas of different organ origins.

TABLE 2

Human Tumor Tissue Immunoperoxidase Staining with the Illustrative Antibody L/1C2

| Tumor | Number Reactive/ Number Tested |
|---|---|
| Lung Squamous Carcinomas | 15/15 |
| Head and Neck Squamous Carcinomas | 12/12 |
| Colon Adenocarcinomas | 17/17 |
| Lung Adenocarcinomas | 7/7 |
| Breast Carcinomas | 9/14 |
| Ovarian Carcinomas | 6/8 |
| Prostate Carcinomas | 4/5 |
| Lymphoma | 0/1 |
| Melanoma | 0/2 |

Evaluation of normal human tissues revealed the L/1C2 antigen was expressed on vessels, ducts, and tubules of several organs including kidney and liver. It is also expressed on the epithelial surfaces of bowel and bronchus. In colon samples containing both tumor and normal tissue, the tumor tissue strained more intensely than did normal colon tissue.

The hybridoma technology originally described by Kohler and Milstein, 1975, Nature 256:495–497 can be used to prepare hybridoma cell lines whose secretory product, monoclonal antibodies, are reactive with the L/1C2 antigen. A general method of preparing these hybridoma cell lines of the invention is described in Example 1, which relates the construction of hybridoma cell line L/1C2, available under accession number ATCC #B9682, from the American Type Culture Collection, Rockville, Md. 20852. Those skilled in the art will recognize that the present invention, including the antibody and hybridoma cell line L/1C2, provide a variety of ways to make the hybridomas, and thus the antibodies of the invention.

The L/1C2 antibody is merely illustrative of the invention, and all antibodies reactive with the L/1C2 antigen, regardless of species of origin or immunoglobulin class or subclass designation including IgG, IgA, IgM, IgE, and IgD are included in the scope of this invention. The present invention also provides antigen-binding fragments of the L/1C2 antibodies. The ability to bind to the L/1C2 antigen is a general characteristic of antibodies of the invention.

As discussed above, antibodies of the invention can be constructed and isolated by immunization, preparation of hybridomas, and identification of antibodies with a reactivity to tumor cell lines and normal tissue distribution similar to that of L/1C2 antibody. However, the present invention also provides a means for identifying antibodies of the invention that does not require determination of antibody reactivity with a broad number of tumor and normal tissues. Antibodies of the invention can be identified by immunoprecipitation and competitive binding studies using the L/1C2 antibody produced by the L/1C2 cell lines.

Similar migration patterns obtained when immunoprecipitations, as described in Example 2, with the L/1C2 monoclonal antibody can be used to identify antigenic identity. Confirmation of identity can be obtained by depleting the antigen from cell extracts using excess amounts of one antibody and observing the inability of the other antibody to immunoprecipitate an antigen from the treated extract. Also, in instances where the antibodies bind to the same epitope or closely associated epitopes, each antibody will compete with the other for binding to the L/1C2 antigen. Competitive binding studies are set forth in Example 4.

Treatment of antibody preparations with proteolytic enzymes such as papain and pepsin generates antibody fragments, including the Fab and F(ab')$_2$ species, which retain antigen-binding activity. Treatment of the antibodies of the invention with such enzymes can therefore be used to generate the L/1C2 binding fragments of the invention. The preparation of antigen binding fragments of the antibodies of the invention and their therapeutic usefulness is illustrated in Example 17. Antigen-binding fragments of the L/1C2 antibody are especially useful in therapeutic embodiments of the present invention.

Those skilled in the art will recognize that the antigen-binding region of the antibodies an antibody fragments of the invention is a key feature of the present invention. The L/1C2 hybridoma cell of the invention serves as a preferred source of DNA that encodes one such antigen-binding region of the invention. This DNA, through recombinant DNA technology, can be attached to DNA that encodes any desired amino acid residue sequence to yield a novel "hybrid", or "chimeric", DNA sequence that encodes a hybrid, or chimeric, protein. In such a fashion, chimeric antibodies of the invention, in which one portion of the antibody is ultimately derived from one species and another portion of the antibody is derived from another species, can be obtained. However, the present invention also comprises any chimeric molecule that contains an L/1C2 antigen-binding region.

The antibodies of the present invention, including the L/1C2 antibody, can be used in immunological assays to diagnose the presence of carcinoma in human tissue samples. Biopsy and necropsy samples of patients can be evaluated for the presence of carcinoma using an L/1C2 antibody of this invention. Antibodies of the present invention can be labeled with detector groups including fluorescent labels enzyme labels, and radioactive labels to identify carcinomas expressing the L/1C2 antigen. Detector groups used in the invention included fluorescein as a fluorescent label, peroxidase as an enzyme label and Iodine-125 as a radioactive label.

Additional fluorescent labels which can be utilized in the invention include, but are not limited to, rhodamine, phycoerythrin and additional compounds emiting fluorescent energy. Additional enzyme labels which can be utilized in this invention include, but are not limited to, glucose oxidase and alkaline phosphatase. Additional radioactive labels which can be utilized in this invention include, but are not limited to, Iodine 131 and Indium-111. One skilled in the art will clearly recognize that these labels set forth above are merely illustrative of the different labels that could be utilized in this invention. L/1C2 antigen-reactive antibodies, can also be derivatized by conjugation to biotin (Example 7), and used, upon addition of species of avidins which have been rendered detectable by conjugation to fluorescent labels enzyme labels or radioactive labels in a multiplicity of immunochemical and immunohistological applications. A method of detecting and diagnosing carcinomas using the antibodies of the invention is illustrated in Example 6.

Characteristics of the L/1C2 antibody include the general characteristic of antibodies of the invention, which is binding to the L/1C2 antigen. The specific characteristics of the L/1C2-reactive antibody produced by hybridoma cell line L/1C2 (ATCC HB9682), include the following physical characteristics: murine IgG3 isotype as determined in Example 8, production as the only immunoglobulin secreted by the L/1C2 cell-line, ATCC accesion number B9682 (see FIG. 1 for SDS-PAGE analysis), and solubility of 10 mg/ml in PBS.

The therapeutic utility of L/1C2 antibody has been established using cytotoxic drug conjugates of this antibody. It has further been established that even unmodified antibody demonstrated in vitro activity. The ability of L/1C2 antibody to inhibit tumor cell growth in vitro is summarized in Table 3. Details of the in vitro tumor cell growth assay are provided in Example 9.

TABLE 3

| | In vitro Tumor Cell Growth Inhibition[1] | | | | |
|---|---|---|---|---|---|
| Concentration | CPM | +/− | S.E. | % Change | P |
| L/1C2 | | | | | |
| 100 μg/ml | 57,144 | +/− | 7,242 | −92 | .001 |
| 10 | 424,406 | +/− | 98,658 | −41 | .05 |
| 1 | 595,578 | +/− | 109,209 | −19 | ns |
| 0 | 736,567 | +/− | 19,026 | | |
| L4/KS | | | | | |
| 100 μg/ml | 698,823 | +/− | 81,625 | −8 | ns |
| 10 | 656,286 | +/− | 43,969 | −13 | ns |
| 1 | 709,928 | +/− | 12,1271 | −6 | ns |
| 0 | 758,271 | +/− | 18,931 | | |
| Bleomycin Sulfate | | | | | |
| 10 μg/ml | 89,906 | +/− | 13,685 | −86 | .01 |
| 0 | 648,327 | +/− | 109,017 | | |

[1]Counts per minute (CPM) of $^3$H-leucine incorporated into T222 squamous carcinoma target cells are indicated. The large number of samples in this assay necessitated using more than 1 tissue-culture plate. Therefore, each test reagent was compared to its own set of negative control wells to calculate percent inhibition. P values were determined using the Student t test. Bleomycin was included in the assay as a positive control.

Table 3 sets forth a comparison of the abilities of L/1C2 antibody and the L4/KS antibody to inhibit in vitro tumor cell growth. Specifically, Table 3 illustrates the ability of unmodified L/1C2 antibody at concentrations as low as 10 μg/ml to significantly inhibit the growth of the L/1C2 antigen positive tumor cell-line, T222. The L4/KS antibody (Starling et al., 1987, *J. Cell Biochem.*, Supplement 11B:192) antibody binds to the KS1/4 antigen, (Varki et al., 1984, *Cancer Res.*, 44:681) is also expressed on the T222 tumor cell-line. The L4/KS antibody in contrast to the L/1C2 antibody was not effective in inhibiting the growth of T222 cells.

In order to understand the novel ability of unmodified L/1C2 antibody to inhibit tumor cell growth, experiments were performed to determine the contributions of complement fixation and antigen internalization. The assay taught in Example 9 was performed using serum which was heated at 56° C. for 30 minutes to cause thermal inactivation of the complement activity. Results of this study indicate that complement fixation did not account for the level of cytotoxicity observed with unmodified antibody. This data is consistent with the data in Table 3 in that L4/KS is an IgG2a isotype, an antibody subclass known to be highly proficient in complement fixation.

Figure 3A:
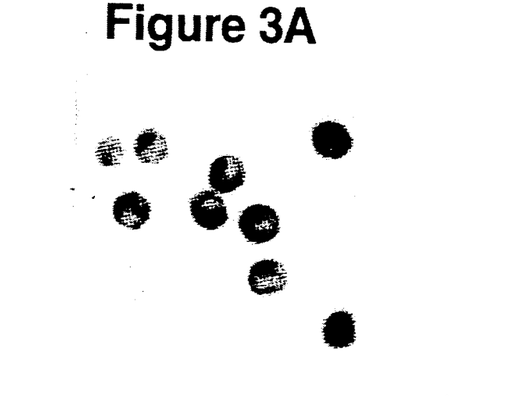
Figure 3B:
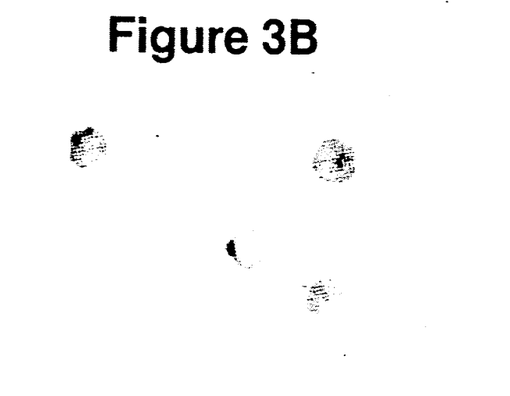
Figure 3C:
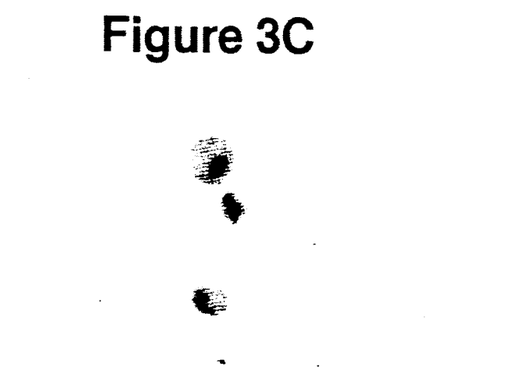

To evaluate the consequences of L/1C2 antibody binding to an antigen positive tumor cell-line, the assays described in Example 10 and 11 were developed. Example 10 teaches the use of fluorescein labeled antibodies reactive with the L/1C2 antigen to evaluate the kinetics of L/1C2 antibody internalization following its binding to the L/1C2 antigen on the cell surface. FIG. 3 depicts the results of this approach to monitoring antibody internalization. It is notable in FIG. 3 that at 0 minutes (Panel A), bright ring-like fluorescence characteristic of membrane topography was evident. In contrast, following 105 minutes incubation at 37° C. (Panel B), ring-like fluorescence was diminished while bright clusters of fluorescence were evident on the periphery of the cell. Finally, at 135 minutes (Panel C), bright ring-like fluorescence was no longer present, but intracellular fluorescence had become evident. The intracellular staining indicates that the L/1C2 antibodies are internalized as a result of binding to the L/1C2 antigen.

Results of the assay described in Example 11 indicated that $^{125}$I labeled L/1C2 antibody was internalized. The use of radiolabeled antibodies to confirm the internalization data from the fluorescent technique of Example 10 was done to discount any role which the cross-linking of cell-surface bound L/1C2 antibodies by the fluorescenated second reagent (anti-mouse immunoglobulin) might have played in inducing internalization. The results of this assay are provided in Table 4. The data of Table 4 clearly demonstrate that L/1C2 is internalized upon binding to the L/1C2 antigen.

TABLE 4

| Evaluation of L/1C2 Anhtibody Internalization Using $^{125}$I-L/1C2 Antibody | | |
|---|---|---|
| | 0° C. mean +/− standard error | 37° C. mean +/− standard error |
| Total cpm of $^{125}$I-L/1C2[1] | 56,770 +/− 3,069 | 56,746 +/− 1,734 |
| non-dissociable counts[2] | 11,398 +/− 859 | 5,514 +/− 64 |

[1]Total cpm of $^{125}$I-L/1C2 is the measurement of total cell associated radioactivity which would include both cell-surface and internalized $^{125}$I-L/1C2
[2]Nondissociable counts are a measurement of the $^{125}$I-L/1C2 which was internalized and therefore was not subject to dissociation by the low pH glycine buffer which is well known to disrupt antigen/antibody binding.

The mechanism by which the L/1C2 antibody inhibits cell growth remains undefined, but it is contemplated that the L/1C2 antigen may be a growth factor receptor. Similar data on internalization and cell growth inhibition using anti-epidermal growth factor receptor (EGF) antibodies have been reported, (Mosui, et al., 1986 *Cancer Res.* 46, 5592) however competitive binding studies and an analysis of cell-line distribution have discounted L/1C2 antibody binding to the EGF receptor.

The significance of an antibody being internalized upon binding to a tumor-cell antigen will be appreciated by those skilled in the art. The effectiveness of an immunoconjugate (antibody-cytotoxic drug) depends in large part upon its ability to target to tumor cells and secondly its ability to present the cytotoxic agent in a toxic form or to release the cytotoxic agent at the tumor site thereby allowing the cytotoxic agent to kill the tumor cells. Internalization of an antibody upon binding to a tumor cell provides intracellular delivery of the cytotoxic agent. This intracellular delivery of a cytotoxic agent would therefore be a preferred delivery system for a cytotoxic agent.

A variety of cytotoxic drugs have been successfully linked to antibodies. Blair et al., 1983, *J. Immunol. Methods* 59, 129 and Ghase et al., 1983, *Methods in Enzymology*, 93 280 review methods of linking cytotoxic drugs to antibodies. The preferred monoclonal antibody-cytotoxic drug conjugates (immunoconjugates) of the present invention comprise those created upon reacting oxidized L/1C2 antibody with hydrazine derivatives of the vinca alkaloids. These potent anti-cancer immuno conjugates are prepared in substantial accord with European Patent Publication No. 247,792, published Dec. 2, 1987, the teachings of which are herein incorporated by reference. The teachings of European Patent Publication No. 247,792 teach construction of immunoconjugates which do not contain the L/1C2 antibody. Example 13 of the instant invention discloses the procedure for attaching vinca hydrazides to the L/1C2 antibody. Reference should be made to European Patent Publication No. 247,792 for a thorough discussion on the preparation of vinca intermediates, the conjugation process, and a discussion of immunoconjugate preparations other than the L/1C2-4-desacetyl-vinblastine-3-carboxyhydrazide used herein as the preferred therapeutic embodiment of the present invention.

L/1C2-4-desacetylvinblastine-3-carboxyhydrazide (L/1C2-DAVLBHYD) or free 4-deacetylvinblasine-3-carboxyhydrazide (DAVLBHYD) or the PBS used as a diluent was administered intravenously to nude mice in the mouse xenograph model described in Example 12. Mice were treated with either L/1C2-DAVLBHYD, DAVLBHYD, or PBS on days 11, 15, 17, 22, 25, and 29 post tumor implantation to generate the data presented in FIG. 4.

Figure 4:
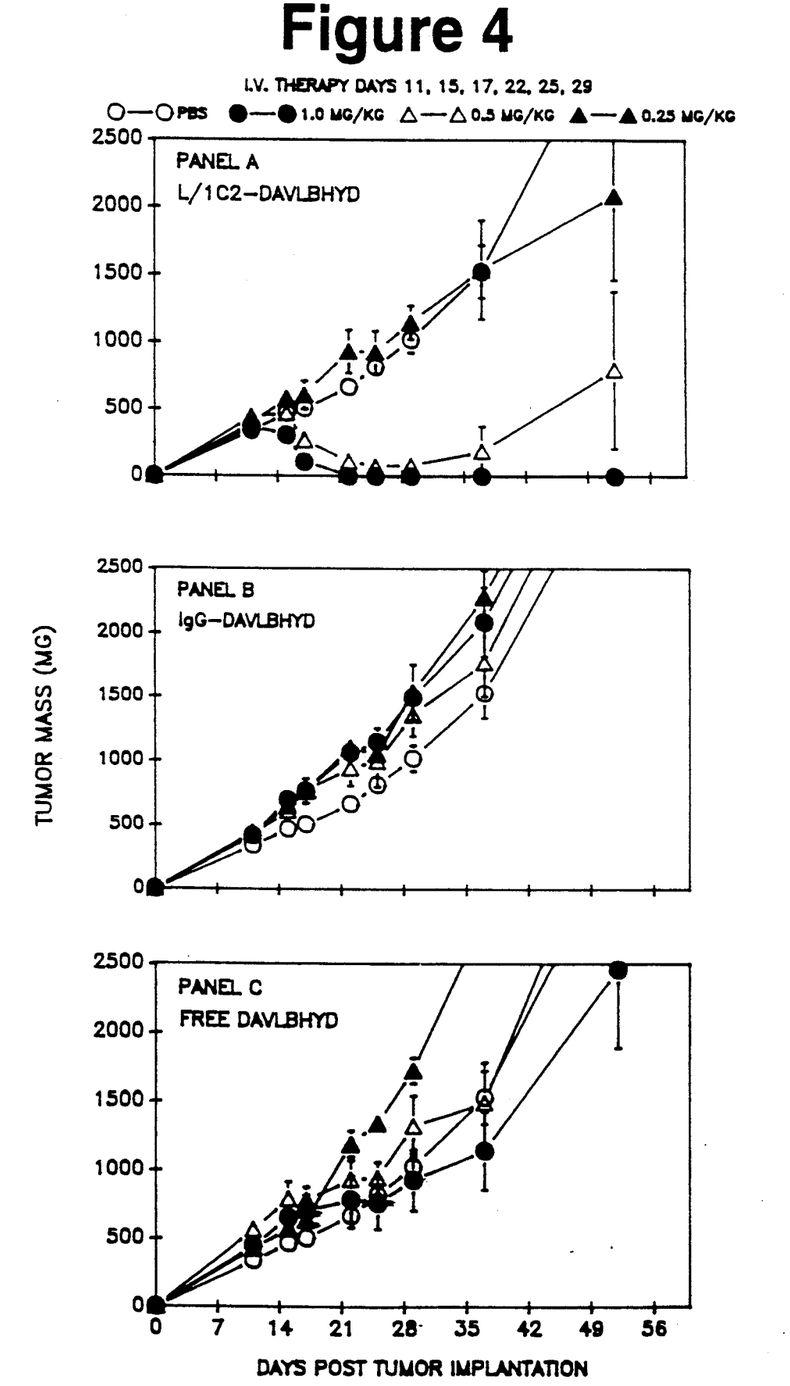

The data of FIG. 4 demonstrates the ability of the L/1C2 antibody to amplify the therapeutic effect of DAVLBHYD. L/1C2-DAVLBHYD conjugates were used in the experiment from which the data of FIG. 4 derives. The L/1C2-DAVLB immunoconjugates were determined to have an average conjugation ratio of 5.7:1 (DAVLBHYD:L/1C2). The dosages described hereinbelow refer to the DAVLBHYD content of the individual treatments. Dosages of 1.0 mg/kg and 0.5 mg/kg DAVLBHYD (Panel A) caused tumor regression when the DAVLB was administered as the L/1C2 DAVLBHYD immunoconjugate (Panel A) while free DAVLBHYD (Panel C) at the same dosage merely retarded tumor growth while therapy was ongoing. The ability of the L/1C2-DAVLBHYD immunoconjugate to eradicate the T222 carcinoma at 1.0 mg/kg vinca content is evident in the upper panel of FIG. 4. A comparison of the relative efficacies reveals that L/1C2-DAVLBHYD is superior to free DAVLBHYD at both the 1.0 mg/kg and 0.5 mg/kg levels throughout the study. Panel B presents data showing that conjugation of DAVLBHYD to an antibody which does not bind to the T222 cells was ineffective in retarding the growth of the T222 cells. L/1C2 antigen reactive immunoconjugates, such as the L/1C2-DAVLBHYD are more effective at suppressing the T222 tumor cell-line than free drug at equivalent dose levels or immunoconjugates which do not react with the L/1C2 antigen. The data as set forth above illustrates the therapeutic role for L/1C2 antigen-binding immunoconjugates.

Further studies have established L/1C2 antibody as a vehicle for delivering other cytotoxic compounds to L/1C2 antigen positive tumor cells. Immunoconjugates were constructed in which methotrexate was coupled to the L/1C2 antibody by both the hydrazide linkage discussed in Example 13 and by the use of linkers to form a hydrolizable bridge between the L/1C2 antibody and the methotrexate. The derivatization of methotrexate to methotrexate-γ-hydrazide is discussed in Example 14, Section A. The methotrexate-γ-hydrazide was conjugated to oxidized L/1C2 antibody in substantial accordance with the teachings of Example 13. The substitution of methotrexate-Y-hydrazide for the 4-desacetylvinblastine-3-carboxyhydrazide of Example 13 resulted in L/1C2-methotrexate immunoconjugates useful for therapeutic applications. These immunoconjugates were evaluated for in vivo anti-tumor activity in the nude mouse xenograft model which is detailed in Example 12. In this study mice were treated with either L/1C2 methotreate-γ-hydrazide, methotrexate, or diluent on days 3, 6, and 9 following tumor implantation. The data appears below in Table 5 and are expressed as a percent of tumor inhibition relative to growth seen in animals treated with diluent alone.

TABLE 5

| In Vitro Activity of L/1C2-Methotrexate-γ-hydrazine Compared to Free Methotrexate | | |
|---|---|---|
| Dosages based on methotrexate content | | Percent Tumor Inhibition |
| L/1C2-methotrexate-γ-hybrid | 6 mg/kg | 97 |
| | 3 mg/kg | 99 |
| | 1.5 mg/kg | 94 |
| Free methotrexate | 6 mg/kg | 32 |
| | 3 mg/kg | −4 |
| | 1.5 mg/kg | 23 |

The results of Table 5 illustrate the increased efficacy of methotrexate when methotrexate is targeted to the tumor site as an L/1C2 antigen reactive immunoconjugate. A conjugation ratio of 5.1:1 moles of methotrexate per mole of L/1C2 antibody was determined for the immunoconjugate by dual wavelength UV analysis at 280 and 370 nm.

Further experiments illustrated the utility of L/1C2 antibody and antigen binding fragments thereof to deliver cytotoxic agents which were covalently attached to the L/1C2 or F(ab¹)₂ fragments thereof via hydrolyzable linkers. Examples 14 through 17 disclose the preparation and evaluation of these immunoconjugates. The chemistry for linking methotrexate-γ-hydrazide to the L/1C2 antibody through the use of linker technology is the subject matter of pending U.S. patent application No. 07/229,941.

The data set forth hereinabove demonstrates the therapeutic utility of the L/1C2 antibody or antigen binding fragments thereof when conjugated to cytotoxic drugs by a variety of linkage techniques. Those skilled in the art will realize that binding to the L/1C2 antigen is a general characteristic of antibodies of the invention and that antibodies of the invention other than those produced by ATCC B9682 would also function to target cytotoxic agents to L/1C2 antigen positive tumors. Variations in the affinities of L/1C2 antigen binding antibodies of the invention should be considered and generally, the higher the affinity of the antibody the more effective the antibody will be to target cytotoxic agents to in vivo tumors. Immunoconjugates comprising the L/1C2 antigen reactive antibody, L/1C2 antibody and derivatives of vinca alkaloids and methotroxate were provided merely to promote the understanding of the therapeutic utility of antibodies of the invention. The therapeutic use of the antibodies of the invention is in no way restricted to those cytotoxic agents used to illustrate the invention. Other cytotoxic agents which would be of use in therapeutic applications of the present invention include, for example, adriamycin, ricin, ricin A chain, diptheria toxin, pseudomonas exotoxin, scirpenol, diacetoxyscirpenol, alphaamanitin, mitomycin C, abrin, gelonin, pokeweed anti-viral protein, 5-fluorouracil, and the like. A variety of other linkage technologies, such as, for example, those disclosed in U.S. Pat: No. 4,671,958 and EPO Publication Number 243,929 are also available for attaching cytotoxic agents to antibodies of the invention and are herein incorporated by reference.

The use of L/1C2 antigen binding monoclonal antibodies of the invention for in vivo tumor imaging is also contemplated in the present invention. Isotopes of elements such as indium, lead, rhenium, technicium, iodine, gallium, leutecium, astatine, bismuth, boron, platinuim, silver, cobalt, yterbium, ruthenium, mercury, scandium, bromine, phosphorous, and yttrium are examples of isotopes which may be used to radioactively label antibodies of the invention.

Radioisotopes such as those set forth above for tumor imaging can be used in therapeutic applications when attached to the L/1C2 antigen binding antibodies of the invention. The use of therapeutic agents consisting of L/1C2 antigen binding antibody-radioisotope immunoconjugates is therefore also contemplated in the present invention.

EXAMPLES

Examples provided are intended to assist in a further understanding of the invention. Particular materials employed, species and conditions are intended to be further illustrative of the invention and are not limiting upon the reasonable scope thereof.

EXAMPLE 1

Construction of L/C12 Reactive Hybridoma Cell lines

A. Immunization

The methodology for monoclonal antibody production was introduced by Kohler and Milstein, Nature 256:495 (1975) and is now well established in the art. A more recent review by Gaflre and Milstein in "Methods in Enzymology" Vol. 73, Langone and Van Vunakis, ed., p. 3–46 (Academic Press, New York, 1981) summarizes improvements of the original method, provides detail on needed equipment and reagents, and describes in detail the steps, to produce the monoclonal antibodies. Selection of an immunogen is limited only to cell lines, tumor samples, or any component thereof containing the L/1C2 antigen.

A cell line of squamous origin, USCLS-1 described by Fernstein, et al., 1986 Cancer Research 46:2970–2977 was propagated in tissue culture and used as a source of L/1C2 antigen. The USCLS-1 cell line is illustrative and any cell-line expressing the L/1C2 antigen (see Table 1) can be used. Young adult BALB/C mice received weekly intraperitoneal injections of $5 \times 10^6$ USCLS-1 cells for four weeks. 21 days after the fourth injection the mice were reimmunized with $5 \times 10^6$ USCLS-1 cells. Mice are illustrative of the method; skilled artisans realize there are no limitations as to the species used as a source of immune cells. Other species, including humans, rats, and hamsters are known to be useful, while in theory any species including rabbit, goat, sheep, pig, chicken and monkey could be used. USCLS-1 cells used as an immunogenic source of L/1C2 antigen were recovered from tissue culture substratum using Trypsin EDTA (Grand Island Biological Company (Gibco), 3175 Staley Road, Grand Island, N.Y. 14072) treatment.

B. Preparation of Splenocytes

Five days following the final immunization, immunized BALB/C mice were cervically dislocated and rinsed in ethanol. Spleens were aseptically harvested and placed in a small sterile dish for splenocyte preparation. Spleens were teased apart, releasing the splenocytes into ice cold Dulbecco's Modified Eagle media (DME-Gibco). Cells were dissociated from clumps by pipetting and transferred to a centrifuge tube, and the tube was placed in ice for five minutes. The sedimented materials were discarded and the cell suspension was transferred into a second tube. Splenocytes were pelleted by centrifugation at 200 g for 5 to 7 minutes. The resulting cell pellet was suspended in 5 ml of ice cold 0.17 M $NH_4Cl$ and placed on ice for 10 minutes to facilitate erythrocyte disruption. 5 ml of ice cold DME were added and the mixture was then centrifuged at 200 g for 5 to 7 minutes. The erythrocyte depleted splenocyte pellet was washed by aspiration of the supernate and resuspended in 10 ml of DME.

C. Preparation of Myeloma Cells

HL-1 TM Friendly myeloma-653 cells (Ventrex Laboratories, P.O. Box 9701, Portland, Me. 04013) were selected for use as a fusion partner for the USCLS-1 reactive splenocyte preparation. These cells were obtained from Ventrex and maintained as per supplier's instructions. Two days prior to fusion, myeloma cells were transferred into 75 cm$^2$ tissue culture flasks to assure log phase growth which is important for successful hybridoma generation.

Although HL-1 TM Friendly 653 cells are the preferred myeloma for cell-fusion, conventional mouse-derived established myeloma cell lines, including P3-X63-Ag8-U1 (P3U1), SP2/0-Ag14 (SP-2), P3-X63-Ag8-6.5.3 (X63.6.5.3), p3-X63-Ag8 (X63), P3-NS-1-Ag4 (NS-1), MPC11-45.6 TG1.7 (MPC-11), and S194/5XXO.BU1 (S194) (see Gaflre and Milstein, 1981, in "Methods in Enzymology" Vol. 73B, Langone and Van Vunakis, ed.) can also be used for purposes of the present invention.

D. Cell Fusion

Splenocytes and myeloma cells were washed by centrifugation at 200 g for 5 minutes at 4° C., followed by aspiration of supernate and resuspension of cells in DME. After 3 DME wash steps, the cells were enumerated and viability was simultaneously evaluated by trypan blue exclusion. As used herein, cell numbers refer only to viable cells (those not stained with trypan blue). $1.5 \times 10^7$ myeloma cells were added to $3.0 \times 10^7$ splenocytes in a 50 cc centrifuge tube. The cells were centrifuged at 200 g for 5 minutes at 4° C., and the supernate was aspirated as completely as possible without loss of cells from the pellet. The cell pellet was then loosened by gently tapping the tube. 1.5 mls of fusing media (formulation below) at 37° C. were added, the contents gently agitated, and the tube left undisturbed for 30 seconds. DME which was warmed to 37° C., was then added dropwise with gentle agitation to slowly bring the contents to a volume of 20 ml. An additional 30 ml of 37° C. DME was added. Caution must be exercised while diluting the mixture to avoid breaking up the cell aggregates. The fusion was centrifuged at 200 g for 5 minutes and gently resuspended into 60 ml of HL-1 TM culture media (Ventrex) containing 20% fetal bovine serum (Gibco) and 1X HAT.

HAT is a mixture of hypoxanthine, aminopterin, and thymidine used to select for splenocyte/myeloma hybrids. Formulations of HAT and PEG 4000 (fusing media) preparation are provided below.

| HAT (100X) | |
|---|---|
| | Amt./25 ml. |
| Hypoxanthine (1000 uM) | 34 mg |
| Aminopterin (100 uM) | 11 mg |
| Thymidine (300 uM) | 18.25 mg |

To prepare, dissolve separately in 1 to 5 drops of 1 N NaOH, mix together, rinse tubes and bring up to 25 ml in DME. HAT is diluted 1:100 in culture media at time of use. HAT is also commercially available from Gibco.

Fusing Medium can be prepared as follows. Autoclave 20 gm PEG 4000 (J. T. Baker Chemical Co., 222 Red School Lane, Phillipsburg, N.J. 08865) in a 100 ml bottle. Add 28 ml sterile Dulbecco's PBS (Gibco) containing 15% DMSO, mix and store at 4° C.

E. Preparation of Feeder Cells 10 ml of ice cold DME was injected into the peritoneal cavity of a BALB/C mouse using an 18 gauge needle. The peritoneal cavity was agitated and the peritoneal wash was removed. The peritoneal cells were placed in an ice cold centrifuge tube and centrifuged at 250 g for 5 minutes. Following supernate aspiration, the cells were resuspended in 2 ml of ice cold HL-1 medium (Ventrex) and placed on ice.

F. Tissue Culture of the Hybridomas

The feeder cells (peritoneal lavaged cells) were combined with the cell fusion mixture and mixed. Two drops per well of the cell mixture were added to 96 well tissue culture plates. A humidified 37° C. incubator with an atmosphere at 5% $CO_2$ was used to maintain the cell-fusion products. The volume of all wells was increased to 200 ul with HL-1 (Ventrex) containing 20% fetal bovine serum (Gibco) and 1X HAT.

G. Selection of Antigen Specific Hybridomas

When macroscopic clones became apparent in the 96 well plates, 50 ul aliquots were removed and evaluated for antigen reactivity. Binding of supernates to USCLS-1, a L/1C2 positive target, and M21, a melanoma derived cell line which is L/1C2 negative, were determined by a radioimmunoassay (RIA) (Morton et al., 1968, Surgery 64(1):233–240)) which is detailed below. Other L/1C2 positive or negative targets could be used and include those in Table 1.

USCLS-1 and M21 cell lines were harvested from tissue culture substratum by CPEG (136 mM NaCl, 2.7 mM KCl, 8 mM $Na_2HPO_4$, 1.5 mM $KH_2PO_4$, 0.5 mM EDTA, 5.6 mM glucose, pH 7.3) treatment for 15 minutes at 37° C. and washed with PBS (Gibco). $1.5 \times 10^5$ cells were dispersed into flexible 96 well plates coated with poly-L-lysine as follows. 50 ul of 1 mg/ml poly-L-lysine hydrobromide (Sigma Chemical Company, P.O. Box 14508, St. Louis, Mo. 63178) made in PBS were pipetted into each well of the plate. The plate was then incubated at least 45 minutes at room temperature, but can be stored at 4° C. Before addition of cells, the plate was rinsed two times with PBS. Cells remaining unattached were washed away with PBS; the remaining cells were fixed with 0.1% glutaraldehyde in PBS. Unreacted glutaraldehyde was blocked with 0.1% glycine, and the plates were washed with and stored in phosphate buffered saline containing 10% fetal bovine serum and $NaN_3$ at 0.05%. Phosphate buffered saline (PBS) is 0.01 M sodium phosphate containing 0.15 M NaCl.

The RIA was done by incubating the hybridoma supernatants with the test cell line for 1 hour at room temperature (approximately 22° C.). Unbound antibody was removed by extensive washing, and 100,000 cpm of $^{125}$I-rabbit anti-mouse IgG, labeled using the Chloramine T method as described by Herzenberg and Herzenberg in "Handbook of Experimental Immunology", 1978, D. M. Weir, ed. Blackwell Scientific Publications, Oxford, were added and incubated an additional hour at room temperature. The wells were washed with PBS and the amount of radioactivity remaining in each well was determined by autoradiography and a gamma counter. Autoradiographic analysis consisted o placing the 96 well plate on x-ray film and noting the well numbers containing sufficient radioactivity to expose the film. The exposure time for the autoradiography varied from 6 hours to overnight. Hybridoma clones producing antibodies reactive with USCLS-1 but not M21 were considered to be of interest and further analyzed. The L/1C2 hybridoma cell line, ATCC #B9862, was USCLS-1 reactive and M21 unreactive. L/1C2 was subcloned two times using a Coulter ® (Coulter Electronics, Hialeh, Fl.) autocloner as per manufacturer's recommendations to ensure the monoclonality of the L/1C2 hybridoma cell line.

H. Determination of Tumor Derived Cell Lines Recognized by L/1C2 Reactive Antibodies L/1C2 is a hybridoma illustrative of the cell lines of the invention. The L/1C2 antibody produced by this hybridoma was evaluated for reactivity against a panel of tumor cell lines. An indirect immuno fluorescence assay was used for screening. The assay mixture consists of: a target cell line being evaluated for the presence of the novel L/1C2 tumor associated antigen, hybridoma supernatant (a source of L/1C2-reactive antibody), and a secondary antibody reagent which is fluorescein labeled and specific for mouse immunoglobulins. Secondary antibody reagents suitable for use are available from multiple vendors such as Jackson ImmunoResearch Laboratories, Inc., P.O. Box 683, Avondale, Pa. 19311, and Miles Research Products, Miles Laboratories, Inc., 1121 Myrtle, Box 2000, Elkhart, In. 46515.

The target cell lines were grown in tissue culture using conditions well established in the art. Prior to assay, the cells were removed from the substratum with Trypsin/EDTA (Gibco). $5 \times 10^6$ cells were washed by centrifugation and resuspension in DME and reacted with hybridoma supernatants in $12 \times 75$ mm tubes for 1 hour at 4° C. The cells were washed free of unreacted antibody by centrifugation through a fetal bovine serum underlay. Target cells were resuspended in a secondary reagent of goat $F(ab')_2$ anti-mouse (IgG+IgM) FITC, (fluorescein isothiocyanate), conjugate (obtained from Tago Laboratories, Burlingame, Ca. 94010) and used at a final dilution of 1:50. The test material was maintained at 4° C. for 1 hour. Target cells were partitioned from the unbound secondary reagent by centrifugation through a fetal bovine serum underlay. The serum was aspirated, and the cells were washed using Hanks balanced salt solution (HBSS) from Gibco. The cells were washed again in HBSS, resuspended in tissue culture medium, and kept at 4° C. for examination by UV fluorescent microscopy. Aliquots of the cells were counterstained with propidium iodide (10 $\mu$g/ml in HBSS) to confirm that antibody stained cells were viable (propidium iodide selectively stains dead cells). Viable cells showing classical surface ring-like fluorescence were considered positive for the L/1C2 antigen.

Alternatively, samples were evaluated for fluorescence with an Epics-Coulter ® Mark IV ® cell analyzer (Coulter Electronics) using methodology well established in the art. Alternative screening strategies for tumor reactive clones are detailed in the teachings of Galfre and Milstein in "Methods in Enzymology" Vol., 73, Langone and Van Vunakis, ed., p. 3–46 (Academic Press, New York, 1981).

I. Evaluation of Human Pathology Specimens Using Antibodies of the Invention Tissue and tumor antigenic distribution were evaluated by an immunoperoxidase procedure using a modification of the avidin-biotin technique. Frozen sections of human tissues were cut at 4–6 $\mu$m onto gelatin coated slides, air dried, and fixed in acetone for five minutes. Following preincubation with 5% horse serum, sections were sequentially incubated with L/1C2 antibody, followed by biotinylated horse anti-mouse Ig (Vectorlabs, Burlingame, Ca.), and a complex of avidin and horseradish peroxidase with washes between steps in phosphate buffered saline, pH 7.2–7.4 containing 1% bovine serum albumin. Optimal dilutions of all components were empirically determined by "checkerboard" titrations as is common in the art. Color was developed using 3,3'diaminobenzidine, and sections were counterstained with hematoxylin. The results of which are summarized in Table 2.

J. L/1C2 Antibody Purification

Following 5 micron filtration, (Millipore) antibody was affinity purified from ascites fluid on a Protein A Sepharose column (Pharmacia Fine Chemicals, Division of Pharmacia Inc., 800 Centennial Avenue, Piscataway, N.J. 08854). The wash buffer was 0.01 M Na phosphate pH 8.0, and elution was carried out using a step gradient with 0.1 M Na phosphate buffer, pH 3.5. Eluted fractions were immediately neutralized with 1 M Trizma buffer (Sigma) pH 7.4 and dialyzed against 0.01 M Na phosphate, pH 7.4 plus 0.15 M NaCl (PBS). Antibody preparations were sterilized by filtration through 0.22 micron filters (Millipore Corporation, Ashby Road, Bedford, Ma. 01730) and stored at 4° C. until used.

K. Production of L/1C2 Antibody

Figure 1A:
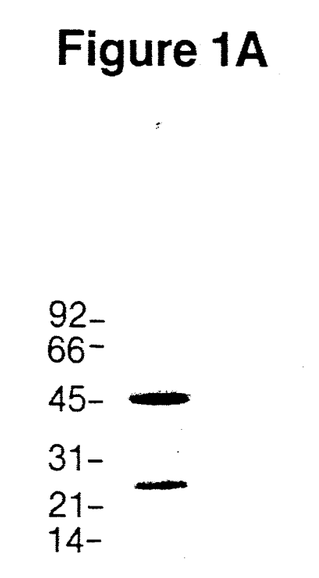

The L/1C2 hybridoma grew well as ascites in pristane-primed BALB/C mice, producing 5–6 mg/ml of antibody. Purification of L/1C2 using Protein A chromatography gave yields in the range of 70–90% and resulted in greater than 90% purity as evaluated by SDS-PAGE, as taught by Laemmli, Nature (London) 227:680, 1970 and Coomassie Blue staining (FIG. 1A). Purified L/1C2 antibody showed excellent solubility in PBS, in which concentrations greater than 10 mg/ml could be achieved without loss through precipitation.

EXAMPLE 2

L/1C2 Antigen Characterization

Characterization of the antigen immunoprecipitated by L/1C2 antibody was determined using radio-labeled 5637 cells (ATCC #HTB9). The cell-line, 5637, is illustrative of L/1C2 antigen positive carcinomas and any of the L/1C2 positive cell lines in Table 1 would be appropriate. The cells were grown in tissue culture to 50–75% confluency, and the attached cells were washed twice with sterile phosphate buffered saline (PBS) pH 7.4 (Gibco). One mCi $^3$H-glucosamine (New England Nuclear, 549 Albany Street, Boston, Ma. 02118, 617-482-9595) was diluted in culture medium and added to the flask. Twenty-four hours later, the metabolically labeled cells were washed twice with cold PBS and extracted for 20 minutes on ice with PBS containing 0.02% sodium azide, 2 mM phenylmethylsulfonyl fluoride, 1% Nonidet® P-40 (Sigma) and 0.1% lauryl sulfate. Following centrifugations at 15,000 g for 15 minutes and at 100,000 g for 1 hour, both at 4° C., the radiolabeled supernatant extracts were stored frozen until used. Prior to use, extracts were incubated with Protein A Sepharose® (Sigma) to remove non-specific binding materials. Indirect immunoprecipitation was carried out by adding up to 50 μg of L/1C2 antibody to 1×10$^7$ CPMs of labeled cell extract and incubating the mixture at 4° C. for four hours. 100 μg of 20% washed Protein A Sepharose® (Sigma) in IP buffer (PBS, 1% BSA, and 0.1% Nonidet P-40®) was then added to the tube, which was then rocked gently for an additional four hours. The complexed antigen, antibody, and Protein A Sepharose® was washed by centrifugation two times with IP buffer, then two times with PBS alone. After the final wash, the pellet was analyzed on SDS-PAGE.

Reference Proteins for the molecular weight determinations of the immunoprecipitated antigen consisted of Lysozyme (14,400), Soybean trypsin inhibitor (21,500), Carbonic Anhydrase (31,000), Ovalbumin (45,000), Bovine Serum Albumin (66,200), Phosphorylase B (92,500), Beta-galactosidase (116,250), and Myosin (200,000). The molecular weight markers used were obtained in kit form from Bio-Rad Laboratories, 2200 Wright Avenue, Richmond, Ca. 94804.

Figure 1B:
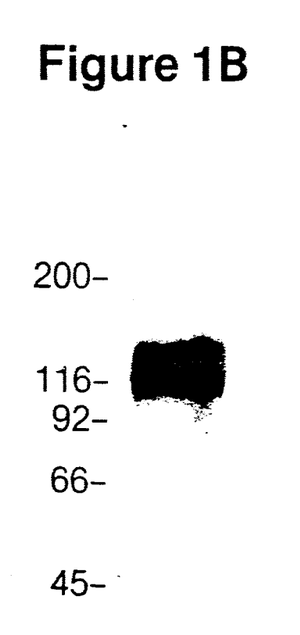

Slab gels containing separated samples were stained with Coomassie Blue to visualize the molecular weight markers and the gels were subsequently subjected to autoradiography to visualize the labeled antigen. (FIG. 1, Paragraph B)

EXAMPLE 3

Production of L/1C2 Antibodies

Vials of frozen L/1C2 hybridomas can be obtained from the American Type Culture Collection, Rockville, Md., under the accession number ATCC #B9682. Viable cells are recovered by thawing vial contents in a 37° C. water bath while swirling the vial to facilitate rapid and uniform thawing. The cell suspension is diluted 1:2 with Balanced Salt Solution (BSS-Gibco) and centrifuged at 200 g through a serum underlay to partition the cells from cryogenic media. Following aspiration of material above the cell pellet, cells are harvested, diluted in tissue culture media supplemented with serum and antibiotics as is common in the art and established in cell culture under standard conditions (37° C. and 5% $CO_2$). During cell culture, it is advisable to maintain the cells at concentrations of $1\times10^5$–$7\times10^5$ cells/ml although modest variances are well tolerated.

L/1C2 antibodies may be recovered from tissue culture in μg/ml quantities. Alternatively, antibody production may be more productively pursued by establishing the L/1C2 as ascites tumors in rodent species. Antibody production and harvesting methods are detailed in an excellent review by Gaflre and Milstein in "Methods in Enzymology", 1981, Vol. 73B, Langone and Van Vunakis, et., p. 43–45 (Academic Press, New York).

EXAMPLE 4

Determination of Antibody Binding to the Antigen of the Present Invention

The determination of whether monoclonal antibodies reacting with L/1C2 antigen positive targets are binding to the L/1C2 antigen is accomplished by either competitive binding experiments or immunoprecipitation analysis. Competitive binding experiments are known to skilled artisans. In this type of experiment an antibody of unknown antigenic specificity is included in an assay wherein a labeled form of L/1C2 antibody is detected. An inhibition of L/1C2 antibody binding would indicate that the antibody in question is binding to the L/1C2 antigen.

A. Competitive Assays

In a competitive radioimmunoassay (RIA), L/1C2 antibodies are prepared and isolated using Protein A chromatography, as detailed in Example 1, and radiolabeled using $^{125}$I in accordance with the teachings of Tsu and Herzenberg in "Selected Methods in Cellular Immunology," ed. Mishell and Shiigi, p. 373–380 (W. H. Freeman and Company, San Francisco). Any of the cell lines expressing L/1C2 antigen as listed in Table 1 are appropriate target cells for the competitive RIA. The L/1C2 antigen presenting cell line is grown in tissue culture until the desired number of cells is attained. Cells are released from cell substratum by CPEG treatment and washed with PBS. $1.5\times10^5$ cells are dispersed into flexible 96 well plates which had previously been coated with poly-L-lysine (Sigma). Cells remaining unattached are washed away with PBS; the remaining cells are fixed with 0.1% glutaraldehyde (2 drops/well for 5 minutes at room temperature). Unreacted glutaraldehyde is blocked with 0.1% glycine, and the plates are washed and stored in PBS containing 10% fetal bovine serum and 0.05% NaN$_3$.

The preparation of target cell plates is described in the teachings of Starling et al., Cancer Research 46(1): 367-374 (1986) and Starling et al., Journal of Supramolecular Structure 11(4): 563-577, 1979, incorporated herein by reference. Optimal dilutions of $^{125}$I-L/1C2 antibody are determined empirically, and the assay is ready for use as a competitive system upon addition of the hybridoma supernates.

Alternative methodology for a competitive assay using $^{125}$I-L/1C2 and hybridoma test samples can be found in teachings of Tsu and Herzenberg in "Selected Methods in Cellular Immunology", ed., Mishell and Shiigi, p. 390-394 (W. H. Freeman and Company, San Francisco).

B. Immunoprecipitation Analysis of Antigen Specificity

Immunoprecipitation of radiolabeled cellular components can also be used to establish whether an antibody reacts with the L/1C2 antigen of this invention. The procedure taught in Example 2 was used to characterize the antigen bound by antibodies of the present invention. A comparison of migration patterns obtained when immunoprecipitation is done with L/1C2 antibody or another antibody will reveal if two different antibodies have antigenic identity. The combination of competitive binding experiments and immunoprecipitation studies provides another means of establishing if antibodies react with the antigen of the invention.

EXAMPLE 5

Production of Polyclonal Antibodies Reactive with the L/1C2 Antigen

Production of conventional antisera to both soluble and particulate (cellular) antigens are well established in the art. Polyclonal antibody production follows injection of foreign matter into any immunologically competent vertebrate species. Ideally, animals serving as producers of the antisera are challenged with antigen repetitively until optimal humoral responsiveness, as measured after trial bleedings, is attained. Any L/1C2 antigen positive material is appropriate for immunization purposes. Reactivity of the resulting antisera towards the L/1C2 antigen can be determined as taught in Example 4.

EXAMPLE 6

Detection and Diagnosis of Carcinomas

The L/1C2 monoclonal antibody, illustrative of antibodies of the invention, was used as a diagnostic tool using a modification of the avidin-biotin immunoperoxidase technique, described by Borowitz, et al., 1983, American Journal of Clinical Pathology 79(3): 387-391.

Frozen sections of tissues were cut at 4-6 um onto gelatin coated slides, air dried, and fixed in acetone for five minutes. Following preincubation with 5% horse serum, sections were sequentially incubated with L/1C2 antibody, followed by biotinylated horse anti-mouse Ig (Vectorlabs) and a complex of avidin and horseradish peroxidase with washes between steps in phosphate buffered saline (PBS), pH 7.2-7.4, containing 1% bovine serum albumin. Color was developed using 3,3'diaminobenzidine and sections were counterstained with hematoxylin.

EXAMPLE 7

Conjugation of Detector Groups to Antibodies of the Invention

The method taught in Example 6 is readily modified to eliminate the need for the second antibody (biotinylated horse anti-mouse Ig) by directly biotinylating the L/1C2 antibody. L/1C2 antibody is purified using Protein A chromatography, desalted into 0.1 M NaHCO$_3$, adjusted to pH 8.5-8.6 with 0.1 M NaHCO$_3$ by dialysis or Sephadex G25 ® (Sigma). Prepared columns of G25 are commercially available from Pharmacia Chemical Co. as PD10 ® columns. L/1C2 antibodies are adjusted to a concentration of 1 mg/ml in 0.1 M NaHCO$_3$, pH 8.5-8.6. N-hydroxysuccinimidobiotin (Pierce Chemical Co., P.O. Box 117, Rockford, Ill. 61105) is rapidly dissolved into DMSO at a concentration of 1 mg/ml, and 120 μl/mg of L/1C2 antibody is added and mixed immediately. The reaction mixture is left at room temperature for 4 hours. The conjugated antibody is separated from unreacted N-hydroxysuccinimidobiotin by either dialysis or passage through Sephadex G25 ®. Detection is facilitated upon reaction of biotinylated L/1C2 antibody with avidin conjugates of fluorescent moieties, radioactive species, or enzymes. The use of avidin-biotin systems of detection is widely exploited in the art and the aforementioned avidin conjugates are commercially available through numerous vendors.

Attachment of fluorescent labels directly to antibodies of the invention can be accomplished by methods set forth in "Selected Methods in Cellular Immunology", 1980, Mishell and Shiigi, ed., Freeman and Company, San Francisco p. 292-302, and herein incorporated by reference.

EXAMPLE 8

Isotype Determination

The isotype of the L/1C2 antibody produced by the L/1C2 hybridoma (ATCC #B9862) was determined to be IgG$^3$. A murine monoclonal sub-isotyping kit obtained from HyClone Laboratories and instructions provided by the vendor were used for this determination.

EXAMPLE 9

In Vitro Tumor Cell Growth Inhibition $1 \times 10^4$ target cells were distributed in each well of 96 well tissue culture plates (Costar) and incubated in leucine deficient medium (leucine free DME plus 13 μg/ml L-leucine, 29.2 μg/ml L-glutamine, 50 μg/ml gentamicin and 10% dialyzed fetal calf serum) for 16 hours at 37° C. in a humidified incubator containing 5% CO$_2$. All tissue culture reagents were obtained from Gibco Laboratories. The medium was then removed aseptically and antibody dilutions were added in 200 μl of leucine deficient medium. The plates were incubated for 48 hours at which time the medium was removed and replaced with leucine deficient media (Gibco) supplemented to achieve 4uCi of $^3$H-leucine (NEN) per well. The plates were returned to the incubator for 24 hours. Radioactivity incorporated into macromolecules was determined using an automated cell harvester and liquid scintillation techniques.

EXAMPLE 10

Internalization of L/1C2 into T222 Tumor cells as Evaluated By UV Microscopy T222 cells were harvested from tissue culture flasks by treatment with Trypsin/EDTA (Gibco) until the cells were observed to detach from the flask. The cells were washed two times with Hanks Balanced Salt Solution (HBSS(Gibco)). 133 $10^6$ cells were transferred to 12×75 mm tubes, pelleted by centrifugation, and the HBSS was aspirated. Fifty µl of L/1C2 (5 µg/ml) was added per tube and incubated on ice for 30 minutes. Following the incubation, the cells were washed two times with HBSS to remove any unbound L/1C2 and following the last wash the HBSS was aspirated. Fifty µl of fluoresceinated goat F(ab')$_2$ anti-mouse IgG (Tago) was added, the contents were then mixed and placed on ice for a 30 minute incubation. The cells were then washed twice with HBSS to remove any unreacted fluoresceinated goat F(ab')$_2$ anti-mouse IgG and this was considered the zero time point of the assay.

EXAMPLE 11

Internalization of L/1C2 into T222 Tumor Cells as Evaluated By $^{125}$I-L/1C2 Endocytosis Purified L/1C2 was labeled with $^{125}$I using Iodobeads (Pierce Chemical Co., Rockford Ill.) according to the manufacturers recommendations. Internalization of $^{125}$I-L/1C2 was evaluated while the cpm in the cell pellet were considered to be internalized $^{125}$I-L/1C2 Malzku et al., 1986, Cancer Research 43:3848. Briefly, 1×10$^6$ target cells were reacted with 200,000 cpm labeled antibody for 90 minutes at 0° C. or 37° C., washed four times, and suspended in 0.5 ml glycine buffer (0.05 M glycine-HCl, pH 2.8 and 0.1 M NaCl) to dissociate cell surface bound immunoglobulin. Following centrifugation, radioactivity in the supernatant or cell pellet was determined. Radioactive counts in the supernatant were considered to be cell-surface bound $^{125}$I-L/1C2.

EXAMPLE 12

Nude mouse Xenograph Screen For Evaluation of Anti-tumor Activity

Outbred nude mice were obtained from Charles River Breeding Laboratories (Boston, Ma.), housed in sterile laminar air flow facilities, and provided sterile water and food ad libitum. Mice approximately two months old were inoculated subcutaneously in the right flank with 1×10$^7$ tumor cells in 0.2 ml PBS. Compounds being evaluated for anti-tumor efficacy were prepared for intravenous administration in sterile PBS and administered with care to minimize animal trauma and infection of the test animals at the injection site.

Efficacy of treatment was determined by monitoring the size of the tumors. Tumor measurements were later taken in two dimensions and the mass was calculated using the formula [(length)(width$^2$)/2]. Inhibition of tumor growth was calculated relative to tumor growth in control animals given PBS alone. Groups of 10 mice were used in all treatment and control groups.

Nude mice are preferred rodents for this test system however, various investigations have reputed immunosuppressing other rodents with either irradiation or immunosuppressants to block host animal immunological responsiveness. T222 cells are an especially preferred human tumor cell-line for the nude mouse xenograft model, however only human tumor cell-line which expresses the L/1C2 antigen and reproducably establishes tumors in nude mice would also be preferred.

EXAMPLE 13

Preparation of L/1C2-4-desacetylvinblastine-3-carboxyhydrazide (A) Oxidation of the L/1C2 antibodies L/1C2 antibody was dialyzed exhaustively in 0.1 M Na acetate buffer pH 5.6 (acetate buffer), diluted to a concentration of 10 mg/ml (total volume was 15.7 ml) and allowed to equilibrate to about 0° C. in an ice water bath. 535 mg of Na periodate (meta) was added as a solid and the reaction mixture was stirred gently until the Na periodate went into solution. Violent stirring was avoided as it would damage the antibody. The reaction mixture was stirred for about 21 minutes in the ice bath while covered with aluminum foil to prevent light from reaching the mixture. Following the 21 minute incubation, 1 µl of 12.5 M ethylene glycol (in water) was added to terminate the oxidation. Aggregated material was removed from the reaction mixture by centrifugation and the clarified solution was chromatographed on a Sephadex G-25 ® gel-filtration column (44 g Sephadex-G25 ®, column 2.5×50 cm) which had been previously equilibrated with acetate buffer. The first peak from the column was collected and diluted to 2.77 mg/ml with acetate buffer. Protein concentration was determined by ultraviolet absorbance of 280 nm, assuming an extinction coefficient of 1.43 for a 1 mg/ml solution of antibody.

(B) Conjugation of oxidized L/1C2 antibody to 4-desacetylvinblastine-3-carboxyhydrazide sulfate To oxidized L/1C2 antibody from step A above (2.77 mg/ml in acetate buffer 55 ml total volume) stirring at about 0°-2° C. was added 238 mg of 4-desacetylvinblastine-3-carboxyhydrazide sulfate (prepared as disclosed in EPO Publication 247,792). When the 4-desacetylvinblastine-3-carboxyhydrazide sulfate dissolved the mixture was wrapped in foil to protect from light and removed to a cold room (4° C.) where it was stirred for about 16 hours. The reaction mixture was then clarified by centrifugation and chromatographed on a Sephadex G-25 filtration column (67 g Sephadex G-25 ®, 2.5×75 cm column, previously equilibrated with PBS. Fractions were collected and the first peak was collected and evaluated for protein and drug concentration using dual-wavelength UV spectroscopy at 280 and 270 nm. Immunoconjugates were stored at 4° C. after sterilization by 0.2 µg filtration (Millipore).

EXAMPLE 14

Preparation of L/1C2 propionyl-3-aminocarbonyl-4-benzaldehyde-methotroxate hydrazide A. Preparation of Methotrexate-γ-hydrazide To a 100 ml flask was added 1.61 g (10 mmoles) of L-glutamic acid, 5-methyl ester. To it was added 60 ml of t-butyl acetate and the mixture was stirred until the compounds were well mixed. To it was then added, dropwise, 1.58 g (11 mmoles) of 70% perchloric acid, with continual stirring. The mixture was allowed to stir under nitrogen for two days, and it was then extracted with 100 ml of 0.5 N hydrochloric acid in three portions. The aqueous layers were combined and neutralized with 30 g of sodium bicarbonate. The neutral solution was extracted with three portions of diethyl ether, 150 ml in total, and the organic layers were combined and washed with brine. The washed organic solution was then dried with sodium sulfate and evaporated at ambient temperature under vacuum to obtain 1.18 g (5.4 mmoles) of a clear oil which was identified as L-glutamic acid, 5-methyl-1-t-butyl diester.

To an oven-dried 100 ml flask were added 0.92 ml (6.6 mmoles) of triethylamine, 1 ml (6.6 mmoles) of diethyl cyanophosphonate and 49 ml of dimethylformamide, freshly distilled under vacuum from barium oxide. To the stirred solution was added 506 mg (1.3 mmoles) of 2,4-diamino-6-[N-methyl-N-(4-carboxyphenyl)amino]-pteridine trihydrate. When the intermediate had dissolved with stirring, the mixture was heated to 80° C., and then 0.20 ml (1.4 mmoles) of triethylamine and 342 mg of the L-glutamic acid diester prepared above were added in 1 ml of dimethylformamide. The mixture was stirred for two hours at 80° C., and was then cooled and the solvent was removed under vacuum. The residue was taken up in 300 ml of chloroform, and was washed with 5% sodium bicarbonate solution. The aqueous layer was extracted with chloroform, and the organic layers were combined, dried over sodium sulfate, and concentrated under vacuum to obtain 1.35 g of orange oil, which was chromatographed on 150 g of silica gel, eluting with 10% methanol in chloroform. The product-containing fractions were combined and concentrated to obtain 645 mg of methotrexate diester, where the $\gamma$-carboxy was in the methyl ester form and the $\alpha$-carboxy was in the t-butyl ester form.

The above intermediate was combined with another lot of the same, making 697 mg (1.3 mmoles) in all, and was dissolved in 12 ml of methanol. To it was added 170 mg (5.3 mmoles) of anhydrous hydrazine, and the mixture was stirred at ambient temperature under nitrogen for six days. Then the solvent was removed under vacuum, and the residue was chromatographed on 150 g of silica gel, eluting with 15% methanol in chloroform, to obtain 470 mg (0.9 mmoles) of methotrexate-$\alpha$-t-butyl ester-$\gamma$-hydrazide.

The above intermediate was dissolved in 120 ml of 1 N hydrochloric acid, and was heated at 55° C. for 50 minutes. It was then concentrated under vacuum to a solid, and the residue was taken up in 80 ml of 0.01 M ammonium acetate at pH 8. The solution was stored for three days at 4° C., and was then chromatographed on 300 ml of Sepharose Fast Flow Q, (Pharmacia, Inc., Piscataway, N.J.) eluting in a gradient manner with the same buffer used immediately above (Buffer A) and 1.0 M ammonium acetate at pH 8 (Buffer B). The product-containing fractions eluting in 100% Buffer B were combined and repeatedly lyophilized to remove traces of ammonium acetate. The yield was 326 mg (0.7 mmoles) of methotrexate-$\gamma$-hydrazide.

B. Preparation of the Linker-3-(4-Formylphenylcarbonyl amino)propionic acid, N-succinimido ester To a 250 ml flask were added 3 g (20 mmoles) of 4-carboxybenzaldehyde and 2.3 g (20 mmoles) of N-hydroxysuccinimide in 100 ml of dioxane. The mixture was stirred for 5-10 minutes, and then 4.1 g (20 mmoles) of dicyclohexylcarbodiimide was added. The mixture was stirred for one hour at ambient temperature, and was then filtered. The filtrate was evaporated under vacuum to obtain 9.4 g of a white solid, which was recrystallized from 25 ml of hot isopropanol. The intermediate product was triturated with isopropanol to obtain 2.1 g (8.5 mmoles) of the desired N-succinimido ester of 4-carboxybenzaldehyde.

Additional batches of intermediate were made, and 10 g (40 mmoles) total of the N-succinimido ester was added to a solution of 3.6 g (40 mmoles) of $\beta$-alanine in 40 ml of 1 N sodium hydroxide and about 100 ml of water. The pH was kept above 8 while the mixture was stirred for 1.5 hours. The mixture was then filtered, and the filtrate was made acid to pH 1.9 with 2 N hydrochloric acid. It was extracted three times with 150 ml total of ethyl acetate, and the organic layers were combined and washed with brine. The organic layer was then dried over sodium sulfate and evaporated under vacuum to obtain 4.6 g (21 mmoles) of a white solid, 3-(4-formylphenylcarbonylamino)propionic acid.

One hundred mg (0.45 mmoles) of the above intermediate, 103 mg (0.5 mmoles) of dicyclohexylcarbodiimide, 57.5 mg (0.5 mmoles) of N-hydroxysuccinimide and 10 ml of dioxane were added to a small flask, and the mixture was stirred at ambient temperature under nitrogen. The progress of the reaction was observed by thin layer chromatography, and 75 mg (0.36 mmoles) of additional dicyclohexylcarbodiimide and 45 mg (0.4 mmoles) of additional N-hydroxysuccinimide were added. After four hours, the reaction mixture was filtered, and the filtrate was evaporated to a solid under vacuum. About 200 mg of impure product was obtained, which was chromatographed on 30 g of silica gel, eluting with 5% isopropanol in dichloromethane. The product-containing fractions were combined and evaporated to obtain 81 mg (0.25 mmoles) of the desired intermediate in somewhat impure form.

C. Coupling the L/1C2 antibody to the linker-propionyl-3-aminocarbonyl-4-benzaldehyde To a 100 ml flask at ambient temperature was added a solution of 1026 mg (6.8 $\mu$moles) of antibody L/1C2 in 76.1 ml of 0.34 M borate buffer at pH 8.6, followed by 14.1 mg (44 $\mu$moles) of the active ester from Preparation 3, in 3.3 ml of acetonitrile. The mixture was stirred for one hour at ambient temperature. It was then chromatographed on 90 g of Sephadex G25 (Pharmacia), eluting with 0.1 M sodium acetate at pH 5.6. The fractions were evaluated by ultraviolet analysis at 258 and 280 nm, and the product-containing fractions were combined to obtain 948 mg (6.3 $\mu$moles) of the desired product, in the form of 111.5 ml of solution having a concentration of 8.5 mg/ml. The conjugation ratio of the derivatized antibody was 4.8 moles of linker per mole of antibody.

D. Conjugation of antibody L/1C2 propionyl-3-amino carbonyl-4-benzaldehyde with methotrexate-$\gamma$-hydrazide A 55.6 ml portion of the product of Preparation 4, containing 472 mg (3.1 $\mu$moles) of the derivatized antibody, was diluted with 87 ml of additional 0.1 M sodium acetate at pH 5.6.

A 101 mg (216 $\mu$moles) portion of methotrexate-$\gamma$-hydrazide was taken up in 7.2 ml of acetonitrile and 21.6 ml of 1 M monobasic potassium phosphate buffer. Approximately 1 ml of 5 N sodium hydroxide was added to the solution, and the solution was then added to the antibody solution. The reaction mixture was made acid to pH 5.8 with glacial acetic acid, and was stirred for 16 hours at ambient temperature. It was then centrifuged, and the supernatant chromatographed on two 90 g Sephadex G25 chromatography columns, eluting with physiological buffered saline.

A total of 202.8 ml of solution was collected from the chromatography, which was analyzed by ultraviolet spectroscopy, observing the spectrum at 280 and 370 nm. Analysis showed that the solution contained 0.018 mg/ml of methotrexate and 1.87 mg/ml of antibody. The conjugation ratio, thus, was 3.0 in molar terms.

The product solution was concentrated by vacuum dialysis against physiological buffered saline in the cold, combining the product solution of this example with 212 ml of product solution from a similar run. The volume was reduced by dialysis to 108 ml.

EXAMPLE 15

Conjugate of antibody L/1C2 propionyl-3-aminocarbonyl-4-benzaldehyde with methotrexate-$\gamma$-hydrazide-modification of reaction conditions to generate conjugates of varying conjugation ratios The conjugation process set forth in Example 14 was repeated four times, under conditions varying from the conditions set forth in Example 14 only as are noted in the following.

A. A 0.67 mg portion of methotrexate-$\gamma$-hydrazide, dissolved in 67 $\mu$l of 0.1 M sodium acetate at pH 5.6 and 33 $\mu$l of acetonitrile, was combined with 1 ml of solution containing 2.2 mg of the intermediate of Example 14, section C in 0.1 M sodium acetate, and the mixture was allowed to stand for 11 hours. It was then chromatographed on 5.9 g of Biogel P6 (Bio-Rad Laboratories, Richmond, Ca. 94804) to obtain 5 ml of conjugate solution, which was found to contain 0.6 mg of the desired conjugate, at a conjugation ratio of 3.2 moles of methotrexate per mole of antibody.

B. The same amount of methotrexate-$\gamma$-hydrazide solution used in Example 15, section A was combined with 0.95 ml of solution of the intermediate of Example 14, section C containing 0.42 mg of the intermediate and the mixture was allowed to stand for 11 hours. It was chromatographed as in Section 15, Section A to obtain 4.75 ml of conjugate solution, containing 0.11 mg of conjugate at a conjugation ratio of 5.4 moles of methotrexate per mole of L/1C2 antibody.

C. 0.7 mg portion of methotrexate-$\gamma$-hydrazide dissolved in 50 $\mu$l of acetonitrile and 100 $\mu$l of 1 M phosphate buffer at pH 5.8 was combined with 2.2 mg of the intermediate of Example 14, section C dissolved in 1 ml of 0.1 M sodium acetate at pH 5.6. The mixture was allowed to stand for 11 hours. It was then chromatographed as in Example 15, section A to obtain 5.3 ml of conjugate solution, containing 1.3 mg of conjugate at a conjugation ratio of 3.3 moles of methotrexate per mole of antibody.

D. 0.7 mg portion of methotrexate-$\gamma$-hydrazide, dissolved in 50 $\mu$l of acetonitrile and 150 $\mu$l of 1 M phosphate buffer at pH 5.8, was combined with 2.2 mg of the intermediate of Example 14, section C, in 1 ml of 0.1 M sodium acetate. The mixture was allowed to stand for 14 hours, and was then chromatographed as in Example 15, section A to obtain 5.3 ml of conjugate solution, containing 1.7 mg of conjugate at a conjugation ratio of 3.3 moles of methotrexate per mole of L/1C2 antibody.

The variations of the conjugation process described above have established a system whereby the extent of drug attachment to the L/1C2 antibody can be controlled. Preferred conjugation ratios are generally considered to be the maximum number of drugs which can be attached without a significant reduction in the antigen binding property of the L/1C2 antibody.

EXAMPLE 16

A. Preparation of the Antibody L/1C2 carbonyl-4-benzaldehyde intermediate

A 0.31 mg portion of 4-carboxybenzaldehyde, N-succinimido ester, was prepared as described in Example 14, section B. It was dissolved in 100 $\mu$l of dimethylformamide and was added to 18.9 mg of antibody L/1C2 in 2.1 ml of 0.34 M borate buffer at pH 8.6. The mixture was stirred for 1.5 hours at ambient temperature, and it was then chromatographed on 6 g of Biogel P6, eluting with 0.1 M sodium acetate at pH 5.6. A 6.2 ml portion of solution was obtained, and was analyzed by ultraviolet, observing the spectrum at 256 and 280 nm. The analysis indicated that 16.1 mg of derivatized antibody was obtained, at a concentration of 2.6 mg/ml, having a conjugation ratio of 5.2 moles of linker per mole of antibody.

B. Preparation of a Conjugate of antibody L/1C2 carbonyl-4-benzaldehyde with methotrexate-$\gamma$-hydrazide Four ml of the solution from Example 16, section A containing 10.4 mg (0.069 $\mu$moles) of derivatized antibody, was combined with 3.2 mg (6.8 $\mu$moles) of methotrexate-$\gamma$-hydrazide in 250 $\mu$l of dimethylformamide. The mixture was allowed to stand for 6 hours at ambient temperature, and was then placed in the refrigerator. After two days, the mixture was centrifuged, and the supernatant was chromatographed on Bio-Gel P6, eluting with physiological buffered saline, to obtain 8.5 ml of solution, which was analyzed by ultraviolet, observing the spectrum at 280 and 370 nm. The analysis showed that the product had a conjugation ratio of 6.4 moles of drug per mole of antibody, and that the solution contained 0.64 mg/ml of conjugate.

The product was evaluated for its ability to inhibit the growth of T222 tumor cells in tissue culture as described in Example 9. It was found that the conjugate produced 70% inhibition of cell growth at 0.035 mcg/ml concentration, based on methotrexate content.

Preparation of L/1C2 antigen binding fragments and conjugates thereof

A. Antibody L/1C2 F(ab')$_2$ fragment

The F(ab')$_2$ fragment of antibody L/1C2 was prepared by adding 2.4 ml of pepsin solution, containing 12.6 mg of pepsin/ml, to 1.5 g of L/1C2 antibody in 270 ml of physiological buffered saline. The mixture was held at 37° C. for 2 hours and 20 minutes, and then the reaction was stopped by the addition of triethanolamine. The product was then concentrated by chromatography on a Sepharose Fast Flow column, eluting with 0.15 M sodium acetate. The F(ab')$_2$-containing fractions were combined, and concentrated by dialysis to obtain 100 ml of product solution containing 992 mg of the F(ab')$_2$ fragment of antibody L/1C2.

Preparation of an Antibody L/1C2 F(ab')$_2$ fragment propionyl-3-aminocarbonyl-4-benzaldehyde intermediate L/1C2 F(ab')$_2$ fragment, prepared in section A of this Example 6, was dialyzed into 0.34 M borate buffer at pH 8.6 to obtain 23 mg (0.23 μmoles) of F(ab')₂ fragment in the form of 3.8 ml of solution. That solution was combined with 0.44 mg (1.4 μmoles) of 3-(4-formylphenylcarbonylamino)propionic acid, N-succinimido ester, in 102 μl of acetonitrile. The mixture was stirred for one hour at ambient temperature, and the solution was then chromatographed over a column of 11 g of Sephadex G25, eluting with 0.1 M sodium acetate at pH 5.6. The product-containing fractions were combined to obtain 19 mg (0.19 μmoles) of derivatized antibody fragment, at a conjugation ratio of 2.8 moles of linker per mole of antibody in 9.6 ml of solution.

C. Preparation of the Conjugate of L/1C2 F(ab')₂ fragment propionyl-3-aminocarbonyl-4-benzaldehyde with methotrexate-γ-hydrazide To 2.7 ml of the derivatized antibody fragment solution prepared as in B above, containing 8 mg (0.08 μmoles) of derivatized antibody fragment, was added 0.47 ml of 1 M phosphate buffer at pH 5.6. To that solution was added 3.7 mg (7.9 μmoles) of methotrexate-γ-hydrazide, dissolved in the minimal amount of 0.1 M sodium acetate. The pH of the mixture was adjusted back to 5.6 with dilute hydrochloric acid, and the mixture was stirred for 17 hours at ambient temperature. It was then centrifuged, and the supernatant was chromatographed on a column of 11 g of Sephadex G25, eluting with physiological buffered saline. Ultraviolet analysis showed that 5.8 mg of conjugate was obtained, in the form of a solution containing 0.95 mg/ml, at a conjugation ratio of 2.1 moles of methotrexate per mole of L/1C2 antibody.

The conjugate was tested in the in vitro tumor cell growth inhibition assay against T222 tumor cells as described in Example 9, and was found to inhibit growth of the cells to the extent of 22% at a concentration of 0.0046 mcg/ml, and to inhibit growth by 83% at a concentration of 0.046 mcg/ml, based on content of methotrexate-γ-hydrazide.

We claim:

1. A tumor-associated glycoprotein antigen in substantially pure form, said antigen having a molecular weight in the range of 110,000–140,000 daltons as determined by using SDS-PAGE under reducing conditions; being present on the surface of human squamous carcinoma cells arising from epithelial cells of the head, neck, and lungs; and being susceptible to immunoprecipitation with the antibody produced by the hybridoma L/1C2, which is ATCC HB9682.

2. A hybridoma cell line that produces an antibody relative with a tumor-associated glycoprotein antigen in substantially pure form, said antigen having a molecular weight in the range of 110,000–140,000 daltons as determined by using SDS-PAGE under reducing conditions; being present on the surface of human squamous carcinoma cells arising from epithelial cells of the head, neck, and lungs; and being susceptible to immunoprecipitation with the antibody produced by the hybridoma L/1C2, which is ATCC HB9682.

3. The hybridoma cell line of claim 2, wherein said antibody is of the class selected from the group consisting of IgG, IgD, IgA and IgM class of antibodies.

4. The hybridoma cell line of claim 3 that is L/1C2, which is ATCC HB9682.

5. The hybridoma cell line of claim 2, wherein said cell line results from the fusion of a myeloma cell with an antibody-producing cell selected from the group consisting of mouse, rabbit, goat, sheep, rat, hamster, pig, chicken, monkey and human antibody-producing cells.

6. The hybridoma cell line of claim 5, wherein said antibody-producing cell is a mouse antibody-producing cells.

7. The hybridoma cell line of claim 6, wherein said antibody-producing cells were derived from mice immunized with human carcinoma cells.

8. The hybridoma cell line of claim 6, wherein said antibody-producing cells were derived from the BALB/C strain of mice.

9. An antibody produced by the hybridoma cell line of claim 2.

10. The antibody of claim 9, wherein the antibody is of a class selected from the group consisting of IgA, IgD, IgG, and IgM class of antibodies.

11. The antibody of claim 10 that is an IgG antibody.

12. The antibody of claim 11 that is the L/1C2 antibody, which is the product of ATCC HB9682.

13. A molecule comprising an antigen-binding region of the antibody of claim 12.

14. A Fab fragment of the antibody of claim 12.

15. A F(ab')₂ fragment of an antibody of claim 12.

16. An antibody reactive with a tumor-associated glycoprotein antigen in substantially pure form, said antigen having a molecular weight in the range of 110,000–140,000 daltons as determined by using SDS-PAGE under reducing conditions; being present on the surface of human squamous carcinoma cells arising from epithelial cells of the head, neck, and lungs; and being susceptible to immunoprecipitation with the antibody produced by the hybridoma L/1C2, which is ATCC HB9682.

17. The antibody of claim 16 that is a chimeric antibody.

18. A molecule comprising an antigen-binding region of an antibody of claim 16.

19. A Fab fragment of the antibody of claim 16.

20. A F(ab')₂ fragment of an antibody of claim 16.

* * * * *

UNITED STATES PATENT AND TRADEMARK OFFICE
CERTIFICATE OF CORRECTION

PATENT NO. : 5,171,666
DATED : December 15, 1992
INVENTOR(S) : Magda C. Gutowski
David A. Johnson It is certified that error appears in the above-indentified patent and that said Letters Patent is hereby corrected as shown below:

At claim 2, line 2, which is column 25, line 51, delete "relative" and insert --reactive-- therefor.

Signed and Sealed this

Twenty-first Day of January, 1997

Attest:

BRUCE LEHMAN

*Attesting Officer*  *Commissioner of Patents and Trademarks*